United States Patent
Van Der Ley et al.

(10) Patent No.: US 7,011,836 B1
(45) Date of Patent: Mar. 14, 2006

(54) MUTANTS OF GRAM NEGATIVE MUCOSAL BACTERIA AND APPLICATION THEREOF IN VACCINES

(75) Inventors: Peter André Van Der Ley, Utrecht (NL); Liana Juliana Josephine Margriet Steeghs, Utrecht (NL)

(73) Assignee: De Staat der Nederlanden, vertenwoordigd door de Minister van Welzijn, Volksgezondheil en Cultuur, HK Rijswijk (NL)

( * ) Notice: Subject to any disclaimer, the term of this patent is extended or adjusted under 35 U.S.C. 154(b) by 0 days.

(21) Appl. No.: 09/486,073

(22) PCT Filed: Aug. 21, 1997

(86) PCT No.: PCT/NL97/00474

§ 371 (c)(1),
(2), (4) Date: Mar. 21, 2000

(87) PCT Pub. No.: WO99/10497

PCT Pub. Date: Mar. 4, 1999

(51) Int. Cl.
*A61K 39/395* (2006.01)
*A61K 39/40* (2006.01)
*A61K 39/00* (2006.01)
*A61K 39/38* (2006.01)
*A61K 39/095* (2006.01)

(52) U.S. Cl. .............. 424/250.1; 424/178.1; 424/184.1; 424/200.1; 424/234.1; 424/250.1; 424/278.1; 424/282.1; 435/41; 435/243; 435/235.1; 435/252.1; 530/388.4

(58) Field of Classification Search .............. 424/1.73, 424/9.2, 203.1, 234.1, 235.1–259.1, 178.1, 424/184.1, 200.1, 278.1, 282.1; 435/72, 435/41, 235.1, 243, 252.1; 514/23; 530/330.1, 530/388.4; 935/65
See application file for complete search history.

(56) References Cited

U.S. PATENT DOCUMENTS 5,527,529 A * 6/1996 Dougan et al. .......... 424/258.1

FOREIGN PATENT DOCUMENTS

| EP | 624376 | * 5/1994 |
| EP | 0 624 376 | 11/1994 |
| WO | WO 97/19688 | 6/1997 |
| WO | WO 97/25061 | 7/1997 |

OTHER PUBLICATIONS

Galloway et al. 1990. 265(11):6394-6402.*
Jennings et al. 1995. Microbial. Path. 19: 391-407.*
Rick et al. 1977. J. of Biol. Chem. 14(25):4895-4903.*
Servos et al. 1996. 175:137-145.*
Verheul et al. 1993. Micro. Rev. 57(1):34-49.*
Vuorio et al. 1995. FEMS Micro. Letters. 134:227-232.*
Ellis, R. 1988. Plotkin & Mortimer Vaccines. Cphapter 29, pp. 568574.*
Boselgo et al. 1991. Vaccines and Immunotheraphy. Chapter 17, pp. 211-233.*
Weinberg et al. 1983. Infect. and Immun. 42(1):219-223.*

* cited by examiner

Primary Examiner—Lynette R. F. Smith
Assistant Examiner—Ja-Na Hines
(74) Attorney, Agent, or Firm—Young & Thompson (57) ABSTRACT

It is possible to inactivate the early stage of lipid A synthesis of mucosal gram negative bacteria without compromising cell viability. In particular the lpxA gene in *N. meningitidis* was mutated and resulting lpxA knockout mutants were found to be completely lipopolysaccharide (LPS)-deficient. The major outer membrane proteins (OMPs) were detected in normal amounts. The finding provides important implications for understanding of structure and biogenesis of the outer membrane. On a practical level, the availability of LPS-deficient mutants of pathogenic mucosal bacteria such as *N. meningitidis* opens up new avenues to vaccine development. It enables easy isolation of endotoxin-free purified proteins, outer membranes or even whole-cell preparations for use in immunisation.

21 Claims, 5 Drawing Sheets fig-2

MUTANTS OF GRAM NEGATIVE MUCOSAL BACTERIA AND APPLICATION THEREOF IN VACCINES

SUMMARY OF THE INVENTION

We found that contrary to previous findings with *E. coli* it is possible to inactivate the early stage of lipid A synthesis of mucosal gram negative bacteria without compromising cell viability. In particular the lpsA gene in *Neisseria meningitidis* was mutated without compromising cell viability. The resulting lpxA knockout mutants were found to be completely LPS-deficient. The major outer membrane proteins (OMPs) were detected in normal amounts. Also, an outer membrane could be discerned in electron micrographs of ultrathin sections. To our knowledge, this was the first instance of a viable Gram-negative bacterial mutant completely lacking in LPS.

The finding provides important implications for our understanding of structure and biogenesis of the outer membrane. On a practical level, the availability of LPS-deficient mutants of pathogenic mucosal bacteria such as *N. meningitidis* opens up new avenues to vaccine development. It enables easy isolation of endotoxin-free purified proteins, outer membranes or even whole-cell preparations for use in immunisation.

BACKGROUND INFORMATION

Lipopolysaccharide (LPS) constitutes the outer monolayer of the outer membrane of Gram-negative bacteria. As such it forms an important component of the outer membrane and has been considered relevant for vaccine purposes (Verheul et al., 1993). The membrane-anchoring lipid A part is responsible for the well-known endotoxin activity of the molecule (Zähringer et al., 1994).

Such endotoxin activity is undesirable in vaccines. Currently some preparations to be used in vaccines are subjected to rigorous, time consuming and costly purification procedures in order to remove this endotoxin activity prior to their being suitable for use as a vaccine. This allows higher doses due to reduced toxicity. However, drastic purification methods can easily lead to denaturation of protein antigens which need to retain their native conformation in order to induce an appropriate immune response. To date Group A and C polysaccharide vaccines are available which have been rendered substantially free of lipo-polysaccharide by means of purification. To date however no whole cell vaccines substantially free of LPS nor OMP vaccines substantially free of LPS have been produced. The following references provide details of processes used to date in order to avoid LPS in pharmaceutical products Akers (1985), Gabler (1987) and the European Pharmacopoeia, 2nd edition "test for non-pyrogenicity". Specifically WIIO Tech. Rep. Ser 594:50 1976 deals with the requirements for a meningococcal polysaccharide vaccine.

Mutants with defects in LPS biosynthesis have been described for many bacterial species however none of these have been considered as candidates for a vaccine free of the endotoxic LipidA. All viable mutants retain a minimal lipid A—KDO structure which is the first part to be synthesised (Raetz, 1990) in LPS synthesis. Thus they would not be suitable to overcome the above-mentioned problem facing vaccine producers. Above all, only conditionally lethal mutations have been reported for genes involved in early steps of lipid A biosynthesis in *Escherichia coli* (Raetz 1990). These mutants have a mutation in genes involved in early steps of lipid A biosynthesis. This finding a suggested that this part of the LPS molecule is in fact essential for bacterial growth. As such this finding would be considered dissuasive by persons skilled in the art of producing vaccines of mutating genes associated herewith as the resulting mutant would not grow. Inhibitors of lipid A biosynthesis have also been found to lead to rapid loss of cell viability in *E. coli* and several other bacteria (Onishi et al., 1996) thus supporting the above-mentioned hypothesis concerning the essential nature of lipid A biosynthesis.

In addition models for biogenesis of OMPs have been proposed in which their correct folding and targeting is dependent on LPS (Sen and Nikaido, 1991; Reid et al., 1990; Laird et al., 1994; de Cock and Tommassen, 1996).

WO 97/25061 discloses mutants of gram-negative bacteria having a form of LPS deficient in levels of myristic acid moiety, in which the lpxF gene is inhibited.

WO 97/19688 describes mutants of gram-negative bacteria producing less toxic LPS as a result of a mutation in the htrB gene.

We previously cloned the lpxA gene from *Neisseria meningitidis* which encodes the enzyme UDP-GlcNAc acyltransferase required for the first step in lipid A biosynthesis (Steegh et al. 1997). While attempting to alter the fatty acyl specificity of this enzyme by constructing an *E. coli-N. meningitidis* hybrid lpxA gene, we made the unexpected discovery forming the basis of the subject invention.

DETAILED DESCRIPTION OF THE INVENTION

The isolation of the *N. meningitidis* lpxA gene involved in lipid A biosynthesis has recently been reported (Steeghs et al., 1997). The deduced amino acid sequence of the LpxA protein showed homology to the *E.coli* acyltransferase responsible for adding the O-linked 3-OH myristoyl chain to UDP-N-acetylglucosamine, which is the first committed step in the lipid A biosynthetic pathway (Anderson and Raetz, 1987; Coleman and Raetz, 1988). Based on this homology and a comparison of the *E.coli* and *N.meningitidis* lipid A structures it is expected that the meningococcal lpxA gene encodes an acyltransferase with 3-OH lauroyl specificity (Kulshin et al., 1992). The basis of the different fatty acid specificity might conceivably be located in the characteristic hexapeptide repeat motif of these acryltransferases which has been determined to play a crucial role in the folding of the *E.coli* protein (Vuorio et al., 1994; Raetz and Roderick, 1995). In an attempt to verify this hypothesis we constructed a hybrid lpxA gene in which the meningococcal N-terminal β-helix domain containing the hexapeptide repeat motif was replaced by the corresponding part of *E.coli* lpxA, followed by transformation and allelic replacement of this construct to *N. meningitidis* H44/76. The experimental data for this are provided in the examples (in particular example 1).

The results demonstrated that strain H44/76[pHBK30] is a viable LPS-deficient mutant. The most likely explanation for this surprising discovery seemed to be that the hybrid lpxA gene had become inactive, either because of disrupted transcription/translation in our construct, or else because of hybrid protein as expressed had lost its enzymatic activity. To discern this, we constructed as lpxA knockout mutant. The results demonstrated once more that blocking of the lipid A biosynthesis pathway in *N. meningitidis* strain H44/76 leads to viable LPS-deficient mutants.

This is the first report of a viable Gram-negative bacterial mutant completely deficient in LPS. It has the following implications:

(1) Surprisingly (in view of the above mentioned view of the essential nature of lipidA biosynthesis for cell viability), it is possible for some gram negative bacteria to make an outer membrane without any LPS yet remain viable. Although our results do not exclude an involvement of LPS in the OMP forming process, they do demonstrate that it obviously cannot be essential. It should be very interesting to study the structure of the outer membrane in the lsxA mutant in more detail.

(2) In *E.coli*, all mutations affecting the early steps of lipid A biosynthesis that have been described are lethal when expressed. The fact that this is not the case in Meningococci opened up the question which organism is typical in this respect, and what causes this difference. Conceivably, it is related to a different LPS-OMP interaction, which is also suggested by the observation that whereas deep-rough LPS mutants of *E.coli* and *Salmonella typhimurium* show a reduced expression of the major OMPs (Koplow and Goldfine, 1974; Ames et al., 1974), a comparable heptose-deficient rfaC mutant of *N.meningitidis* was found to have normal expression of the class 1 and 3 porins (Hamstra and van der Ley, unpublished).

We postulate that mucosal gram negative bacteria can in an analogous manner be mutated thereby becoming free of endotoxic LPS. Subsequently enabling development of LPS free whole cell or acellular vacines such as OMP vaccines. The basis for this postulation is found in the knowledge available to the skilled person concerning the Lipid a biosynthesis in mucosal gram negative bacteria. FIG. 6 e.g. as derived from Raetz 1990 provides a diagram of the early steps in lipid A biosynthesis. It reveals the requirement of lpxA and lpxB as enzymes required in the early biosynthesis. The enzyme lpxD is also known to be involved (Steeghs et al 1997). Knowledge of the nucleic acid sequences encoding these genes is available to the skilled person (Steeghs et al 1997). Subsequently mutating one or more of the genes encoding the enzymes involved in the early stages of LipidA biosynthesis is possible. FIG. 6 shows the early stages; preferably the mutation will arise such that no stage leading past the lpxB stage is reached as these products already closely resemble Lipid A structure. Preferably the mutation will arise as early as possible in the biosynthesis pathway. In most cases the genes encoding lpxA, lpxB and lpxD are clustered. Steeghs et al provides references disclosing such details for *Escherichia coli, Salmonella typhimurium, Yersinia entereocolitica, Haemophilus influenzae* and *Richettsia rickettsii*. Knowledge of the sequence of these microorganisms is thus available to the person skilled in the art and homologous sequences in other organisms can be found. Both lpxA and lpxD contain a characteristic hexapeptide repeat structure $[(I,V,L)GXXXX]_n$. The lpxB gene is generally cotranscribed with lpxA and as such can also be readily found. The cluster also comprise the fabZ gene which can also be used to ascertain the location of the gene cluster involved in Lipid A biosynthesis (Steeghs et al. 1997). Steeghs et al provide the genbank number under which the *N.meningitidis* sequence data concerning the Lipid A biosynthesis gene cluster is available i.e. U79481. The other references mentioned therein covering sequences of other organisms are also incorporated by reference.

There are two possibilities to mutate one or more genes associated with LipidA biosynthesis. Such mutation can be either such that enzyme is produced in an inactive form or such that the gene is mutated such that it is not expressed i.e. thereby forming a socalled knockout mutant. The manners in which this objective can be achieved are numerous and will be readily available to a person skilled in the art of genetic engineering. Clearly by way of example of such a manner the analogous procedure to that employed in the examples can be used for different microorganisms and/or different enzymes known to be involved in the early stages of Lipid A biosynthesis. The principal of preparing knockout mutants in general is well known and can be applied to any of the genes encoding enzymes active in the early stages of Lipid A biosynthesis.

The subject invention comprises the mutants described above. In addition it comprises new vaccines made from such organisms or component parts thereof. Such new vaccines are free of Lipid A. Such vaccines can in fact be completely free of either active or inactive Lipid A. As a consequence the vaccines are free of LPS. The Limulus test can be applied as described herein to ascertain that a preparation is in fact free of LPS.

Thus a vaccine against a gram negative mucosal bacterium said vaccine being substantially free of LPS, wherein substantially free can be ascertained by the Limulus test, said vaccine comprising a microorganism according to the invention as disclosed above as active component falls within the scope of the invention. This is a so called whole cell vaccine. In addition a vaccine against a gram negative mucosal bacterium comprising one or more components of the aforementioned microorganism which is also substantially free of LPS as defined above is covered by the invention. In particular an OMP comprising vaccine substantially free of LPS as defined above is covered by the invention.

A method of producing a vaccine against gram negative mucosal bacteria employing a microorganism according to the invention and/or parts derived therefrom as active component in a manner known per se for producing whole cell or acellular vaccines is covered by the invention as are the products of said method. The vaccines according to the invention will preferably be further characterised by the presence of an adjuvant to enhance the immunogenic activity thereof. A number of adjuvants commonly used in vaccines are known. Any of these can be suitably applied. Any dosage form and additional components commonly used for vaccines, in particular meningococcal vaccines is suitable for the subject invention.

Particularly suited target microorganisms are diplococci and *Bordetellla pertussis.* The diplococci comprise meningococci and gonococci. Examples of each category are *N.meningitidis* and *N. gonorrhoeae.* Numerous other organism falling within this category are known from Bergeys Handbook of Determinative Bacteriology. These dipolcocci are structurally closely related and show the same gene structure. Both are interesting microorganisms from a vaccination view point as are a number of other microorganisms such as *Haemophilus influenzae* and *Moraxella catarrhalis.*

Clearly, the construction of lpxA knockout mutants can be attempted in other bacterial species known to the have LipidA in their lipopolysaccharide.

(3) The availability of LPS-deficient mutants will allow new approaches to vaccine development against *N.meningitidis* and the closely related pathogen *N.gonorrhoeae,* as well as any other bacteria as mentioned above for which such mutants can be made and isolated. First, it will become much easier to purify OMPs or other cell surface components without contaminating endotoxin. Secondly the role of LPS in meningococcal outer membrane vesicle vaccines, e.g. as adjuvant or in stabilising OMP conformation (Verheul et al., 1993; Nakano and Matsuura, 1995; Poolman, 1995), can now be unequivocally determined and possibly taken over by a less toxic compound. Thirdly the use of inactivated whole cell vaccines can be investigated using endotoxin-free mutants according to the invention such as the lpxA mutants. Finally, the possibility to use LPS-deficient strains as live attenuated vaccines now rises.

The exact nature of the invention will be further elucidated with the following examples.

EXAMPLE 1

Construction of an inactive lpxA gene in N.meningitidis

In two separate PCR reactions the *E.coli* and *N.meningitidis* part of the hybrid gene were amplified with the Epri1/Epr2 and Npr1/Npr2 primer, respectively (FIG. 1). The inside primers Epr2 and Npr1 were designed so that the ends of the products complementary sequences. These products were mixed, denatured and reannaeled in a second PCR in which the fused construct was amplified by the outside primers Epr1 and Npr2, having an MluI and SpeI site respectively (FIG. 1). The resulting PCR product was cloned and its sequence verified.

To test the activity of the hybrid lpxA, this gene was used to replace the original lpxA in the meningococcal chromosome (FIG. 2). For this purpose the 1.0 kb MluI/SpeI fragment carrying the wildtype lpxA gene in plasmid pLA19 (a pUC18 derivative with a 1.9 kb lpxD-fabZ-lpxA insert) was replaced by the similarly digested hybrid lpxA gene. Subsequently, a kanamycin-resistance cassette was ligated into the MluI site located directly upstream of lpxA, resulting in the plasmid pHBK30.

Transformation of *N.meningitidis* H44/76 with linearized pHB30 yielded kanamycin-resistant colonies after 24 hours of incubation. These mutants died when transferred to fresh GC plates with kanamycin (100 μg/ml).

By reducing the kanamycin concentration and screening of the resulting colonies by PCR amplification of lpxA hybrid-specific fragments we finally succeeded in the isolation of viable kanR± H44/76[pHBK30] transformants in which the chromosomal lpxA gene had been replaced by the hybrid construct as shown in FIG. 2.

LPS of the H44/76[pHBK30] mutant and the wildtype strain was compared by Tricine-SDS-PAGE followed by a silver stain for carbohydrates (FIG. 3). Surprisingly, no LPS could be detected in the hybrid derivative by this method, even when higher amounts of cell lysates were loaded on the gel.

To get more insight into the structure of the outer membrane of H44/76[pHBK30] a panel of LPS and OMP specific mAbs was tested in a whole cell ELISA (Table 1). The mutant strain did not bind any of the LPS-specific mAbs, whereas the OMP-specific mAbs showed similar binding patterns for mutant and wildtype. This apparent OMP similarity was confirmed when OMCs of H44/76[pHBK30] and H44/76 were isolated and analysed by SDS-PAGE (FIG. 3). Both strains show equal amounts of the class 1, 3 and 4 OMP; in contrast to the wildtype, the mutant apparently also expresses a class 5 OMP.

Since LPS of H44/76[pHBK30] could not be detected with any of the methods described above, it become questionable whether it was present at all. Therefore, the mutant and wildtype strain were tested in a chromogenic Limulus (LAL) assay, with meningococcal medium as a negative control. This assay depends on activation of the clotting enzyme cascade in amoebocyte lysate prepared from the horseshoe crab and is capable of detecting picogram quantities of endotoxin. The results of the LAL assay on cell suspensions showed no significant endotoxin activity for H44/76[pHBK30] over meningococcal medium (0.3 and 1.7 EU/ml, respectively), in contrast to $21.7\times10^4$ EU/ml for the wildtype.

Taken together, these results demonstrate that the initial attempt to replace the wildtype lpxA gene with the hybrid construct resulted in the isolation of what was apparently an LPS-deficient mutant. This was further confirmed by gas-chromatography/mass-spectrometry (GC-MS) analysis of fatty acids present in OMC preparations, which showed that the lipid A-specific 3-OH C12 was present only in trace amounts in the mutant. As this fatty acid is added in the first step of lipid A biosynthesis, its absence demonstrates that the mutant is truly LPS-deficient and not just making some incomplete precursor molecule with no antibody binding or LAL assay activity.

Although H44/76[pHBK30] is fully viable, a reduced growth rate compared to the wildtype strain was apparent. When grown overnight on GC agar plates, the mutant strain produced much smaller colonies; in liquid medium the doubling time during exponential growth was approximately 50% higher than in wildtype strain H44/76.

The morphology of H44/76[pHBK30] and its parent strain was examined by electron microscopy of ultrathin sections. In contrast to the wildtype, cells of H44/76 [pHBK30] were more heterogeneous in size and a significant fraction showed signs of lysis. However, the outer membrane could be clearly discerned in the LPS-deficient mutant (FIG. 5). In contrast to the somewhat "baggy" appearance in the wildtype, the outer membrane of the mutant showed a "tighter fit", possibly indicating a lowered rate of synthesis.

EXAMPLE 2

Construction of an lpxA knockout mutant

An lpxA knockout mutant of *N.meningitidis* was constructed by inserting a kanamycin-resistance cassette into the BstEII site located at position 293 within the lpxA gene of plasmid pLA21 (a pUC18 derivative with a 2.1 kb lpxD-fabZ-lpxA insert). The resulting plasmid pLAK33 was digested with XbaI/SacI and transformed to strain H44/76 with selection for kanamycin-resistance. As expected, the resulting colonies showed the same growth properties as the H44/76[pHBK30] mutant, indicating the lack of LPS. This was confirmed by a whole cell ELISA in which the lpxA knockout mutant did not bind any of the LPS-specific mAbs. These results demonstrated once more that blocking of the lipid A biosynthesis pathway in *N. meningitidis* strain H44/76 leads to viable LPS-deficient mutants.

DETAILED DESCRIPTION OF THE METHODS AND STRAINS USED IN THE EXAMPLES

Where no specific details are provided standard technology has been applied. Where references are provided the content thereof is to be considered incorporated herein.

Bacterial Strains and Plasmids

The *E.coli* strains NM522 and INVαF' were grown on LB medium at 37° C. The *N.meningitidis* strain H44/76 and its derivatives were grown at 37° C. on GC medium base (Difco) supplemented with IsoVitaleX (Becton Dickinson) in a humid atmosphere containing 5% $CO_2$, or in liquid medium as described (van der Ley et al., 1993). For selection of meningococcal transformants (van der Ley et al., 1996kanamycin was used in a concentration of 75–100 μg/ml. With *E.coli*, antibiotics were used in the following concentrations: ampicillin, 100 μg/ml; kanamycin, 100 μg/ml. For cloning of PCR fragments, the TA cloning kit with the vector pCRII (Invitrogen) was used. Another vector used was pUC18.

Recombinant DNA Techniques

Most recombinant DNA techniques were as described in Sambrook et al. (1989). Plasmid DNA was isolated using the pLASmix kit (Talent). The polymerase chain reaction (PCR) was performed on a Perkin Elmer GeneAmp PCR system 9600 with Taq polymerase. Sequence analysis was performed with an Applied Biosystems automatic sequencer on double-stranded plasmid DNA templates (isolated with Qiagen columns) and with a cycle sequencing protocol.

LPS Analysis

Tricine-sodium dodecyl sulphate polyacrylamide gel electrophoresis was performed in 4% stacking and 16% separating gels as described by Lesse et al. (1990). Proteinase K-treated, boiled bacterial cells were used as samples. The gels were run for 17 h at a constant current of 20 mA, and silver stained by the method of Tsai and Frasch using the QCL-1000 kit from BioWhittaker Inc. (Walkersville, Md., USA) according to the instructions of the manufacturer. Overnight cultures were diluted in meningococcal medium to an OD at 620 nm of 0.1, and serial dilutions of these stocks were used as samples in the LAL assay. For fatty acid analysis by GC-MS, OMC samples were acetylated for 3 h at 90° C. in pyridine and acetic acid anhydride in order to completely dissolve the LPS. The samples were subsequently heated for 3 h at 65° C. in tetrahydrofuran in the presence of $LiAlH_4$ to reduce the O-linked fatty acids to the free alcohols. These were derivatized to TMS-ethers for 1 h at 60° C. with BSTFA+1% TMCS in pyridine, and analyzed by GC-MS on an Autospec (Micromass, Manchester, UK) in the electron impact mode. The amount of 3-OH C12 in the samples was quantified using 2-OH C12 as internal standard.

Characterization of OMP Composition

Binding of mAbs specific for class 1, 3 and 4 OMPs and for the oligosaccharide part of immunotype L3 LPS was tested in a whole-cell ELISA (van der Ley et al., 1995, 1996). Isolation of OMCs by sarkosyl extraction and their analysis by SDS-PAGE were done as described previously (van der Ley et al., 1993).

REFERENCES

Figure 1:
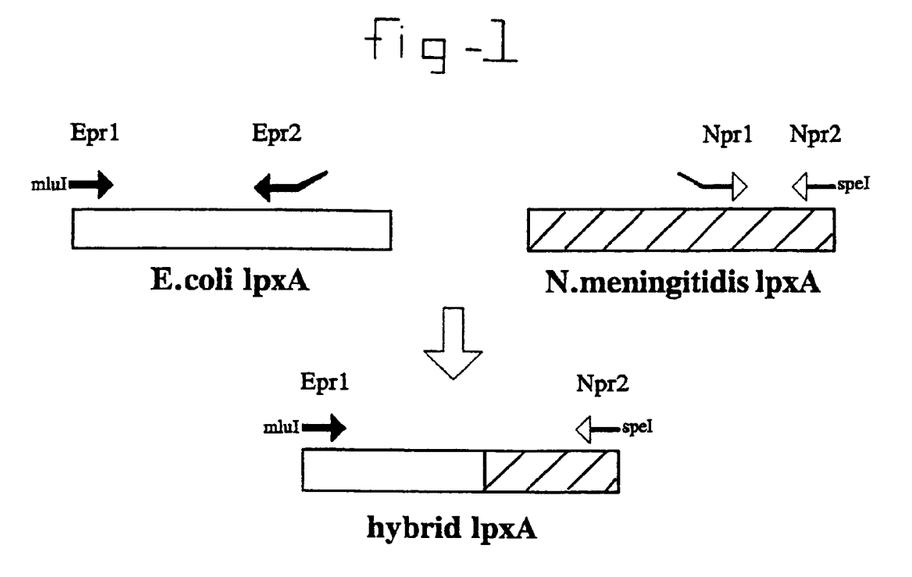
FIG. 1. Constructions of H44/76[pHBK30]. Two-step PCR mutagenesis leading to the hybrid lpxA gene, with *E.coli*-specific primers Epr1 (ACT-GACGCGTGTGAT-TGATAAATCCGC) SEQ ID NO:1 and Epr2 (GTAGGGCGGCACGTCCTGCGCCACACCGGA) SEQ ID NO:2 and *N.meningitidis*-specific primers Npr1(TCCG-GTGTGGCGCAGGACGTGCCGCCCTAC) SEQ ID NO:3 and Npr2 (CGGCCGCTCTAGAACTAGTGGATCA) SEQ ID NO:4.
Figure 2:
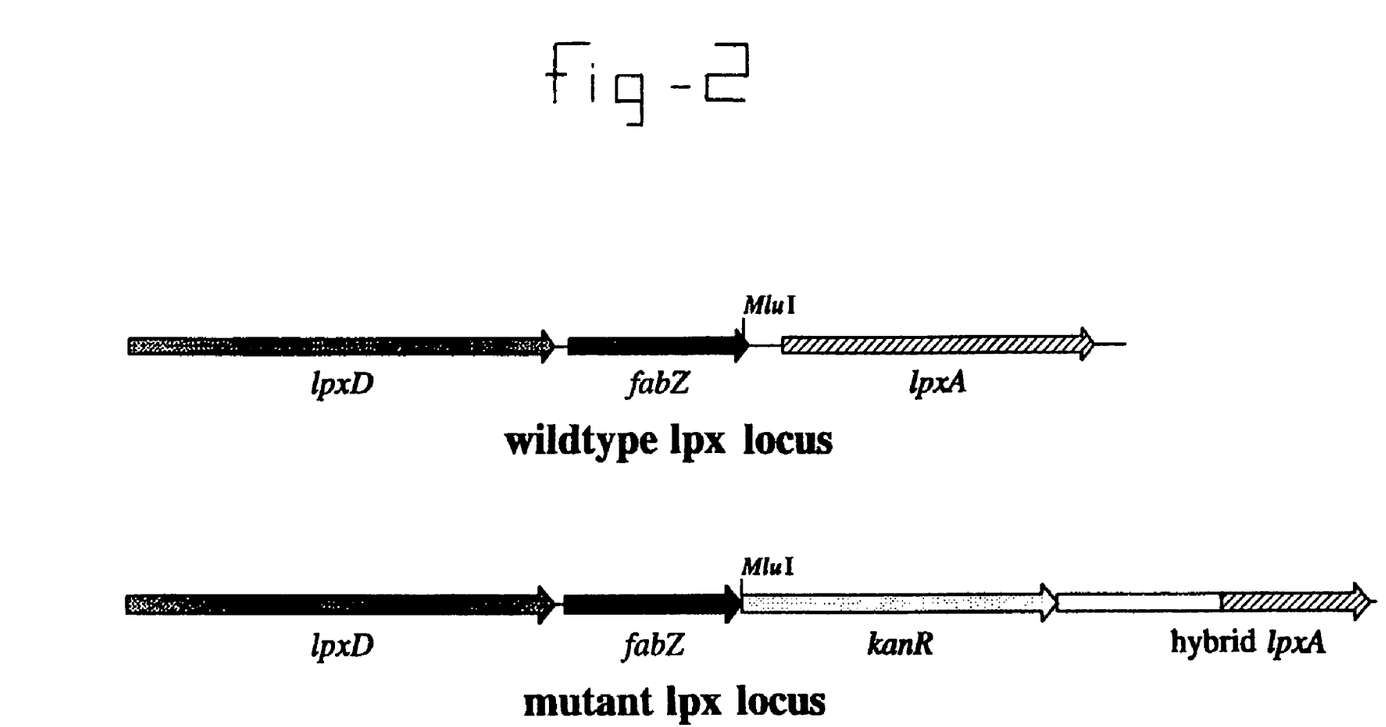
FIG. 2. Construction of H44/76[pHBK30]. Replacement of the chromosomal lpxD-fabZ-lpxA locus with the pHBK30 insert, carrying in addition to the *E.coli-N.meningitidis* hybrid lpxA gene a kanR selection marker instead of the 99 bp region between the MluI site in fabZ and the start codon of lpxA.
Figure 3:
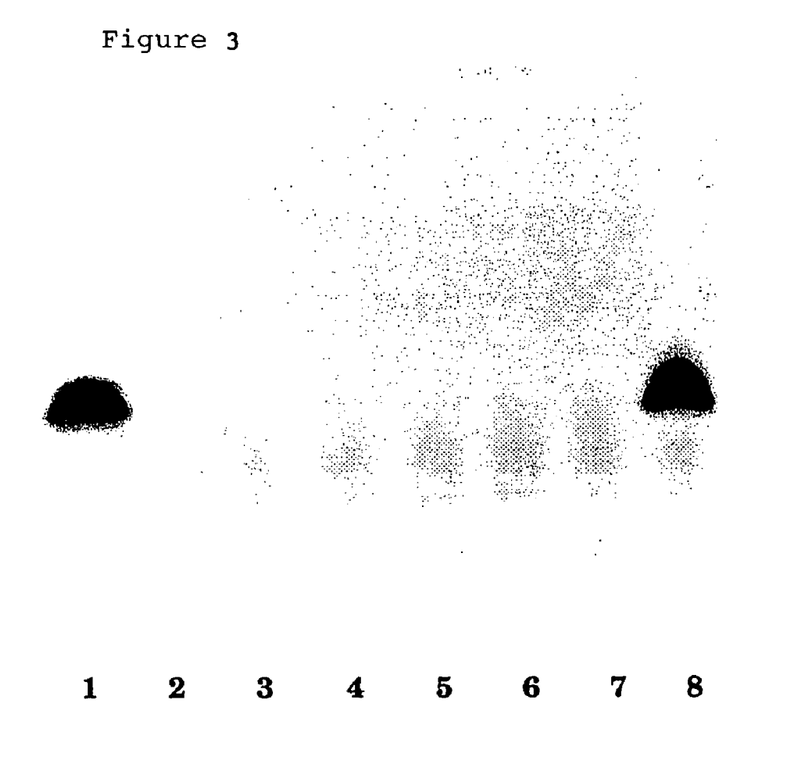
FIG. 3. SDS-PAGE analysis of H44/76[pHBK30]. Silver-stained Tricine-SDS-PAGE LPS gel of proteinase K-treated whole-cell lysates of H44/76 (lanes 1 and 8) and six independent kanamycin-resistant transformants with pHBK30 (lanes 2–7).
Figure 4:
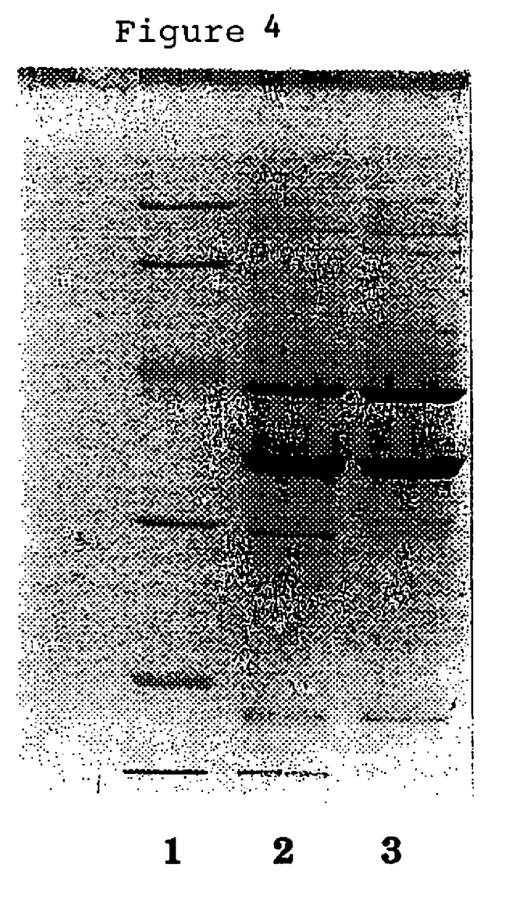
FIG. 4. SDS-PAGE of OMC proteins from H44/76 [pHBK30] (lane 2) and H44/76 wildtype (lane 3): lane 1 contains a molecular weight marker of 94, 67, 43, 30, 20.1 and 14.4 kDa.
Figure 5:
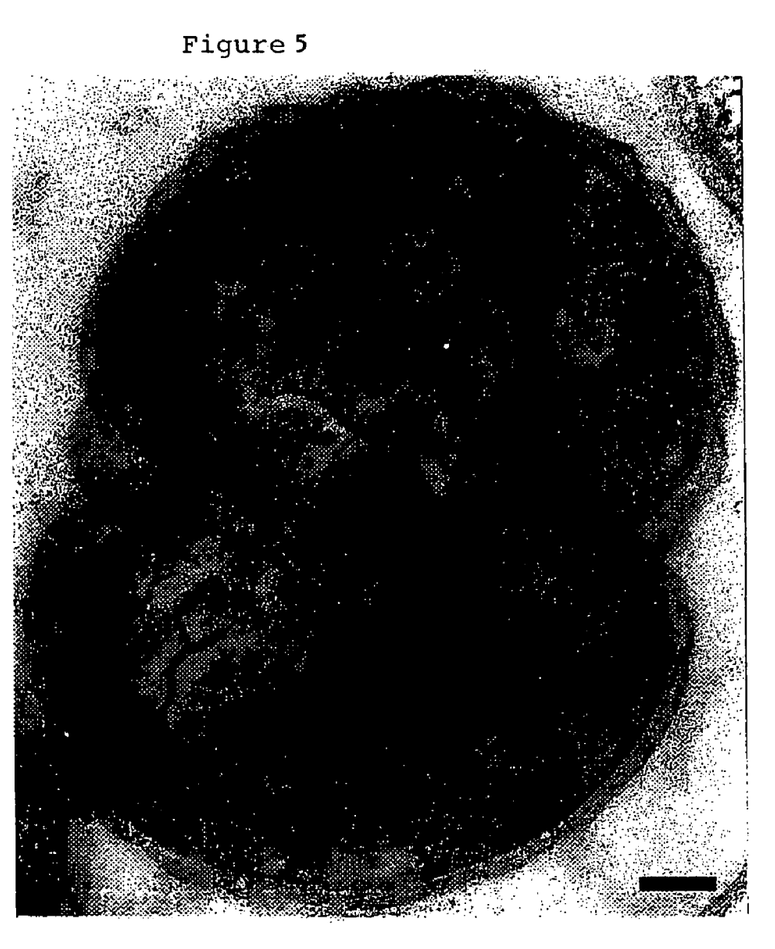
FIG. 5. Electron micrograph of an H44/76[pHBK30] thin section, showing the presence of the outer membrane in the absence of LPS.

Akers, M. J. Parenteral Quality Control. Chapter 2: Pyrogen Testing. Marcel Dekker, Inc. New York and Basel, 1985, pp. 79–142.

Ames, G. F.-L., Spudich, E. N. and Nikaido, H.: Protein composition of the outer membrane of *Salmonella typhimurium*: effect of lipopolysacharide mutations. J Bacteriol. 117 (1974) 406–416.

Anderson, M. S. and Raetz, C. R. H: Biosynthesis of lipid A precursors in *Escherichia coli*. A cytoplasmic acyltransferase that converts UDP-N-acetylglucosamine to UDP-3-O-(R-3-hydroxymyrisotyl)-N-acetylglucosamine. J. Biol. Chem. 262 (1987) 5159–5169.

de Cock, H. and Tommassen, J.: Lipopolysaccharides and divalent cations are involved in the formation of an assembly-competent intermediate of outer-membrane protein PhE of *E.coli*. EMBO J. 15 (1996) 5567–5573.

Coleman, J. and Raetz, C. R. H.: First committed step of lipid A biosynthesis in *Escherichia coli:* Sequence of the lpxA gen e. J. Bacterial. 170 (1988) 1268–1274.

Gabler, F. R. Pyrogens, nd the depyrogenation of solutions with ultrafiltration membranes. In: Meltzer, T. H. Filtration in the pharmaceutical industry. Marcel Dekker, Inc. New York and Basel, 1987, pp. 919–939.

Karnovsky, M. J.: Use of ferrocyanide-reduced osmium tetraoxide in electron microscopy. Proc. 11th Ann. Meeting Soc. Cell Biol. 51 (1971) 146.

Koplow, J. and Goldfine, H.: Alterations in the outer membrane of the cell envelope of heptose-deficient mutants of *Escherichia coli*, J. Bacteriol. 117 (1974) 527–543.

Kulshin, V. A. Zähringer, U., Linder, B., Frash C. E., Tsai, C., Dimitriev, A. and Rietschel, E. T.: Structure characterization of the lipid A component of pathogenic *Neisseria meningitidis*, J. Bacteriol. 174 (1992) 1793–1800.

Laird, M. W., Koser, A. W. and Misra, R.: Assembly of LamB and OmpF in deep rough lipopolysaccharide mutants of *Escherichia coli* K-12, J. Bacteriol. 176 (1994) 2259–2264. Lesse, A. J., Campagnari, A. A., Bittner, W. E. and Apicella, M. A.: Increased resolution of lipopolysaccharides and lipooligosaccharides utilising tricine-sodium dodecyl sulfate-polyacrylamide gel electrophoresis, J. Immunol. Meth. 126 (1990) 109–117.

van der Ley, P., van der Biezen, J., Hohenstein, P., Peeters, C. and Poolman, J. T.: Use of transformation to construct antigenic hybrids of the class 1 outer membrane protein in *Neisseria meningitidis*. Infect. Immun. 61 (193) 4217–4224.

van der Ley, P., van der Biezen, J. and Poolman, J. T.: Construction of *Neisseria meningitidis* strains carrying multiple chromosomal copies of the porA gene for use in the production of a multivalent outer membrane vesicle vaccine. Vaccine 13 (1995) 401–407.

van der Ley, P., Kramer, M., Steeghs, L., Kuipers, B., Andersen, S. R., Jennings, M. P., Moxon, E. R. and Poolman, J. T.: Identification of a locus involved in meningococcal lipopolysaccharide biosynthesis by deletion mutagenesis. Mol. Microbiol. 19 (1996) 1117–1125.

Nakano, M. and Matsuura, M.: Lipid A. In: Stewart-Tull, D. E. S. (Ed.), The Theory and Practical Application of Adjuvants. John Wiley & Sons, 1995, pp. 315–335.

Onishi, H. R., Pelak, B. A., Gerckens, L. S. et al.: Antibacterial agents that inhibit lipid A biosynthesis. Science 274 (1996) 980–982.

Poolman, J. T.: Development of a meningococcal vaccine. Infect. Agents Dis. 4 (1995) 13–28.

Raetz, C. R. H.: Biochemistry of endotoxins, Annu. Rev. Biochem. 59 (1990) 129–170.

Raetz, C. R. H. and Roderick, S. L.: A left-handed parallel β helix in the structure of UDP-N-Acetylglucosamine acyltransferase. Science 270 (1995) 997–1000.

Reid, G., Hindennach, I. and Henning, U.: Role of lipopolysaccharide in assembly of *Escherichia coli* outer membrane proteins OmpA, OmpC and OmpF. J. Bacteriol. 172 (1990) 6048–6053.

Steeghs, L., Jennings, M. P., Poolman, J. T. and van der Ley, P.: Isolation and characterization of the *Neisseria meningitidis* lpxD-fabZ-lpxA gene cluster involved in lipid A biosynthesis. Gene 190 (1997) 263–270.

Tsai, C. M. and Frasch, C. E.: A sensitive silver stain for detecting lipopolysaccharides in polyacrylamide gels. Anal. Biochem. 119 (1982) 115–119.

Verheul, A. F. M., Snippe, H. and Poolman, J. T.: Meningococal lipopolysaccharides: Virulence factor and potential vaccine component. Microbiol. Rev. 57 (1993) 34–49.

Vuorio, R., Härkönen, T., Tolvanen, M. and Vaara, M.: The novel hexapeptide motif found in the acryltransferase LpxA and LpxD of lipid A biosynthesis is conserved in various bacteria. FEBS Lett. 337 (1994) 289–292.

Zähringer, U., Lindner, B. and Rietschel, E. Th.: Molecular structure of lipid A, the endotoxic center of bacterial lipopolysaccharides. In: Horton, D. (Ed.), Advances in Carbohydrate Chemistry and Biochemistry, vol. 50. Academic Press Inc. San Diego, 1994, pp. 211–276.

SEQUENCE LISTING

```
<160> NUMBER OF SEQ ID NOS: 4

<210> SEQ ID NO 1
<211> LENGTH: 27
<212> TYPE: DNA
<213> ORGANISM: Escherichia coli

<400> SEQUENCE: 1
actgacgcgt gtgattgata aatccgc                                          27

<210> SEQ ID NO 2
<211> LENGTH: 30
<212> TYPE: DNA
<213> ORGANISM: Escherichia coli

<400> SEQUENCE: 2
gtagggcggc acgtcctgcg ccacaccgga                                       30

<210> SEQ ID NO 3
<211> LENGTH: 30
<212> TYPE: DNA
<213> ORGANISM: Neisseria meningitidis

<400> SEQUENCE: 3
tccggtgtgg cgcaggacgt gccgccctac                                       30

<210> SEQ ID NO 4
<211> LENGTH: 25
<212> TYPE: DNA
<213> ORGANISM: Neisseria meningitidis

<400> SEQUENCE: 4
cggccgctct agaactagtg gatca                                            25
```

Sambrook, J., Fritsch, E. F., and Maniatis, T.: Molecular Cloning: A Laboratory Manual. Cold Spring Harbor Laboratory Press, Cold Spring Harbor, New York, 1989.

Sen. K. and Nikaido, H.: Lipopolysaccharide structure required for in vitro trimerization of *Escherichia coli* OmpF porin. J. Bacteriol. 173 (1991) 926–928.

The invention claimed is:

1. A viable bacterium of the species *Neisseria meningitidis,* comprising a mutation in an lpxA gene, wherein said mutation causes the bacterium to lack endotoxic lipopolysaccharide (LPS).

2. The bacterium according to claim 1, wherein the bacterium lacks Lipid A.

3. An immunogenic composition comprising a bacterium according to claim 1, or a component part of the bacterium as active component.

4. The composition according to claim 3, wherein the bacterium is a live attenuated bacterium.

5. The composition according to claim 3, wherein the component part of the bacterium is an outer membrane vesicle, an outer membrane complex or an outer membrane protein.

6. The composition according to claim 3, wherein the composition is substantially free of endotoxic LPS as determined with a Limulus assay.

7. The composition according to claim 3, wherein the composition further comprises an adjuvant.

8. A method for producing an immunogenic composition comprising culturing a bacterium according to claim 1, isolating the bacterium in a LPS culture and incorporating the bacterium, as an active component into said composition to produce an immunogenic composition.

9. The method according to claim 8, further comprising incorporating an adjuvant into said composition.

10. A method for producing an LPS-free outer membrane protein from *Neisseria meningitidis* comprising culturing a bacterium according to claim 1, isolating outer membrane proteins from the culture, testing the outer membrane isolated proteins to determine whether the outer membrane proteins are free of LPS, and recovering LPS-free outer membrane proteins from the culture.

11. A viable bacterium of the species *Neisseria meningitidis,* comprising an inactive lpxA gene or an lpxA knock-out mutant with an lpxD-fabZ-lpxA insert.

12. The bacterium according to claim 11, wherein the bacterium lacks Lipid A.

13. An immunogenic composition comprising a bacterium according to claim 11, or a component part of the bacterium as active component.

14. The composition according to claim 13, wherein the bacterium is a live attenuated bacterium.

15. The composition according to claim 13, wherein the component part of the bacterium is an outer membrane vesicle, an outer membrane complex or an outer membrane protein.

16. The composition according to claim 13, wherein the composition is substantially free of endotoxic LPS as determined with a Limulus assay.

17. The composition according to claim 13, wherein the composition further comprises an adjuvant.

18. A method for producing an immunogenic composition comprising culturing a bacterium according to claim 11, testing the culture to determine whether said culture contains LPS-free bacterium, isolating said bacterium, and incorporating the bacterium, as an active component into said composition.

19. A method according to claim 18, further comprising incorporating an adjuvant into said composition.

20. A method for producing an LPS-free outer membrane protein from *Neisseria meningitidis* comprising culturing a bacterium according to claim 11 isolating outer membrane proteins from the culture, testing the outer membrane isolated proteins to determine whether the outer membrane proteins are free of LPS, and recovering an LPS-free outer membrane proteins from the culture.

21. An immunogenic composition comprising a bacterium according to claim 11.

* * * * *